United States Patent [19]
Nishida et al.

[11] Patent Number: 5,996,403
[45] Date of Patent: Dec. 7, 1999

[54] METHOD AND APPARATUS FOR EVALUATING THE SAGGING CONDITIONS OF A SEALANT

[75] Inventors: Tsuyoshi Nishida; Takuto Oka, both of Hiratsuka, Japan

[73] Assignee: The Yokohama Rubber Co., Ltd., Tokyo, Japan

[21] Appl. No.: 09/034,898

[22] Filed: Mar. 4, 1998

[30] Foreign Application Priority Data

Mar. 5, 1997 [JP] Japan .................................. 9-067313

[51] Int. Cl.$^6$ .................................................. G01N 33/44
[52] U.S. Cl. ...................... 73/53.01; 73/866; 73/150 R
[58] Field of Search ............... 73/53.01, 150 R, 73/866

[56] References Cited

FOREIGN PATENT DOCUMENTS

| 61-122544 | 6/1986 | Japan | .................... 73/150 R |
| 214868 | 3/1968 | U.S.S.R. | .................... 73/866 |

OTHER PUBLICATIONS

"Car Manufacturing Specification Evaluation Method" JASO M 338–89, Japanese Automobile Standards Organization.

*Primary Examiner*—Daniel S. Larkin
*Attorney, Agent, or Firm*—Finnegan, Henderson, Farabow, Garrett & Dunner, L.L.P.

[57] ABSTRACT

A method and apparatus for measuring the sagging conditions of a sealant. The method is conducted by filling up a sealant in a retaining device, bringing the sealant into contact with a contacting device, moving the retaining device and/or the contacting device reciprocally and linearly to apply shear stress on the sealant and then separating the retaining device and the contacting device from each other to observe the shape of the sealant. The apparatus essentially comprises a retaining device for holding a sealant therein and a contacting device brought into contact with the sealant and a controlling device for moving the retaining device and the contacting device reciprocally and linearly.

8 Claims, 2 Drawing Sheets

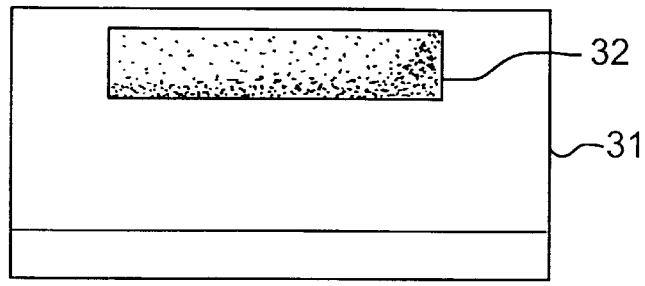
FIG. 2a
PRIOR ART
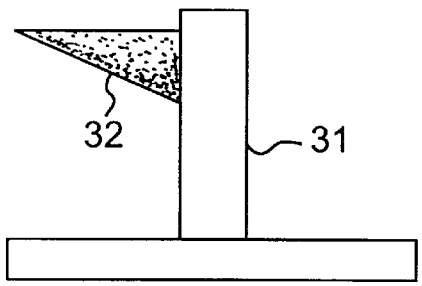
FIG. 2b
PRIOR ART
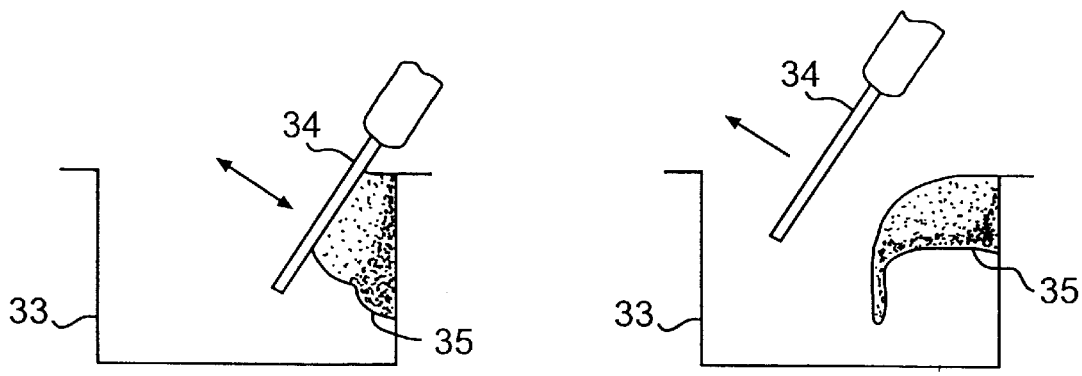
FIG. 3a
PRIOR ART
FIG. 3b
PRIOR ART

METHOD AND APPARATUS FOR EVALUATING THE SAGGING CONDITIONS OF A SEALANT

BACKGROUND OF THE INVENTION

1. Field of the Invention

This invention relates to a method and apparatus for evaluating the sagging properties of a sealant with thixotropy included.

2. Prior Art

A sealant used in the car manufacturing industry is imparted with thixotropic properties so that the sealant can maintain its shape upon application until being cured. The sealant is used in the process of fitting a glass sheet, such as a windshield, to an automotive body in which process the sealant is applied in the form of a triangle-shaped bead to the window frames and then the windshield is fitted thereon. The reason for applying the sealant in a form of the triangle shaped bead rather than a round shape in section is that the sealant can secure fixedly to the windshield on the window frame in a smaller amount. More specifically, the portion of the window frames where the windshield is to be fixed is a groove that is concave in section. If a sealant rounded in section is applied onto the groove, it makes contact with the upper walls of the groove and thus fails to be applied into the groove completely, leading to the necessity of pressing the sealant into the groove and application of an extra amount of the sealant so as to maintain the windshield in position sufficiently. On the contrary, a sealant in the shape of a triangle can be put into the groove by inserting it from the tip or corner until it reaches the bottom of the groove and thus can be applied in larger amounts than the rounded one, thereby obtaining a sufficient sealing effect. Therefore, a sealant is required to be imparted with thixotropy to maintain this shape when being applied.

The criterion of thixotropy to be imparted differs depending upon the usage of a sealant. There is one conventional method known as "Car Manufacturing Specification Evaluation Method" stipulated as JASO M 338-89 by the Japanese Automobile Standards Organization which can evaluate the sagging conditions of a sealant.

In this method, a sample sealant (32) is coated in the shape of a triangulated bead onto a glass sheet (31) and held vertically in a standing position for 30 minutes, followed by observing the level of sagging of the sealant (32) as shown in FIGS. 2a and 2b.

However, this method fails to provide precise evaluation because of not conforming to a real automotive production line where a sealant is automatically applied to automotive bodies by means of a plurality of nozzles, but is kneaded before arriving at the site where the nozzles are located. The sealant is supplied from a vessel, such as a drum, by means of a pump through a plurality of pipes and, thus, is subjected to shear stress until being discharged from the nozzles, effecting adversely the sagging conditions. The sealant once affected by shear stress is seemingly in the softened state and prone to sag upon application to an automotive body. However, the evaluation of the above-mentioned method results from a sample sealant which is not subjected to kneading and thus, does not encounter sagging as experienced in a real automotive production line. Therefore, this method can not evaluate the sagging conditions of a sealant in conformity with a real production line.

There is another conventional method for evaluating the sagging conditions of a sealant known as "Developing Department Shear Method". In this method, a sealant (35), in a predetermined amount, is coated onto a side wall of a polyethylene cup (33) as shown in FIG. 3a. The sealant is then applied with shear stress using a spatula (34) a predetermined number of times for a predetermined period of time and thereafter, followed by examining the shape of the sealant after pulling out the spatula therefrom as shown in FIG. 3b thereby evaluating the sagging conditions of the sealant (35). However, this method also is accompanied with a problem because when an operator applies shear stress on the sealant (35) manually using the spatula (34), it is extremely difficult to apply It repeatedly with the same degree of shear stress even though a single operator conducts the method. Furthermore, in the case where shear stress is applied by more than two operators, the resulting data are scattered due to the different criteria depending upon each operator.

SUMMARY OF THE INVENTION

With the foregoing drawbacks of the prior art in mind, the invention seeks to provide a method and apparatus which can evaluate the sagging conditions of a sealant, practically, in conformity with a real automotive production line.

More specifically, the invention provides a method for evaluating the sagging conditions of a sealant with thixotropy, wherein the sealant is held in a retaining means including an opening through which the sealant is filled up, facing the horizontal direction and brought into contact with a contact means positioned in opposed relation thereto; and then shear stress is applied onto the sealant by reciprocal linear movement of the retaining means and/or the contacting means, repeated a predetermined number of times for a predetermined period of time, followed by examining the shape of the sheared sealant after separating said retaining means and the contacting means from each other The invention further provides an apparatus for evaluating the sagging conditions of a sealant which comprises: a retaining means supported so as to be capable of reciprocal and linear movement in a horizontal direction and including an opening facing one of the directions of reciprocal movements, the sealant being held in the retaining means; a contacting means supported so as to be capable of reciprocal and linear movement on an extension of the line along which the retaining means reciprocates so that it can be brought into contact with the sealant held in the retaining means; and a driving device moving the retaining means and the contacting means reciprocally and linearly so as to apply shear stress on the sealant, and then separating the retaining means and the contacting means from each other.

BRIEF DESCRIPTION OF THE DRAWINGS

FIGS. 2a and 2b show a prior art method for evaluating the sagging conditions of a sealant; and FIGS. 3a and 3b show another prior art method for evaluating the sagging conditions of a sealant.

DETAILED DESCRIPTION OF THE INVENTION

Figure 1:
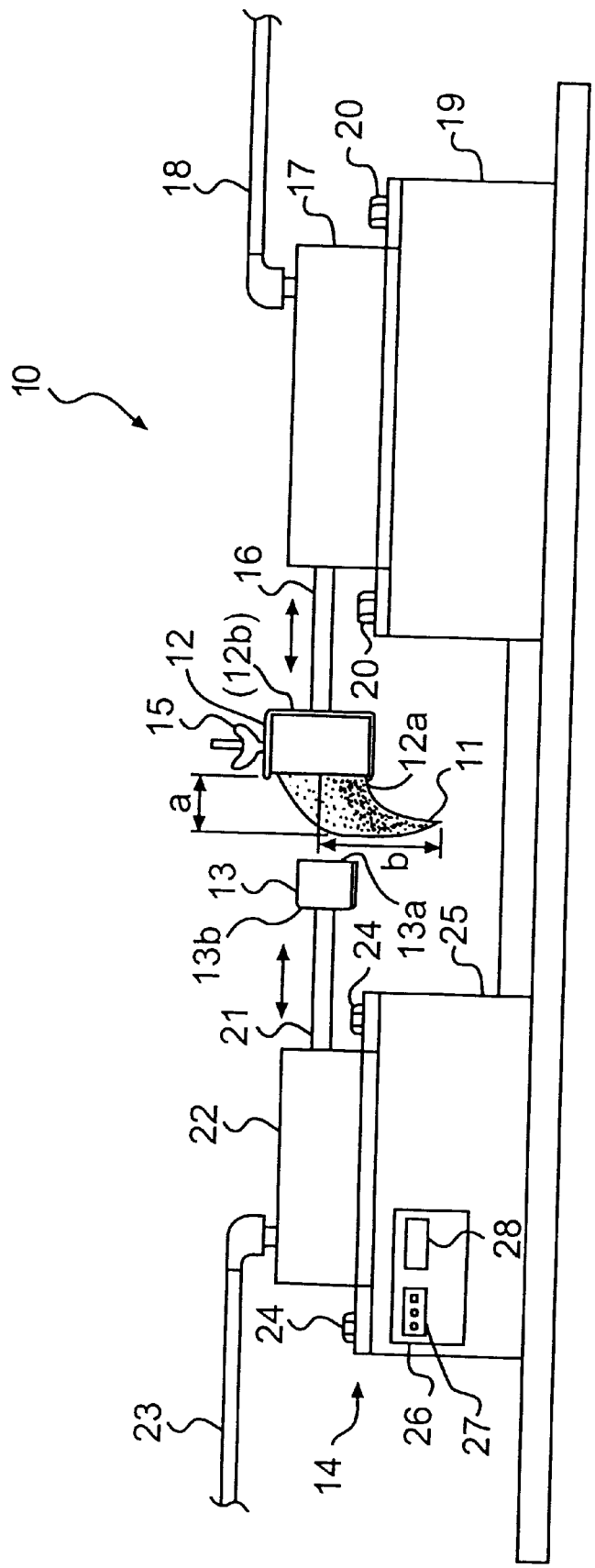
FIG. 1 shows an embodiment of an apparatus according to the invention.

In FIG. 1, indicated by numeral (10) is a test apparatus for measuring the sagging conditions of a sealant (11), which apparatus comprises essentially: a retaining means (13) holding the sealant (11) therein, a contacting means (12) brought into contact, therewith, and a driving means (14) applying shear stress on the sealant (11) by moving the retaining means (12) and the contacting means (13) back and forth.

The sealant (11) is applied to vehicles, such as automobiles, and may be any type of sealant as long as it has thixotropy.

The retaining means (12) includes an opening that may be cylindrical or polygonal. In this figure, there is employed a cylindrical retaining means (12). The retaining means (12) may be filled up with the sealant (11) as it is. Alternatively, the retaining means (12) may have thereinside a vessel (not shown) into which the sealant (11) is filled, fixed by suitable means such as a screw (15). The apparatus shown in FIG. 1 is a type using the vessel. The sealant (11) may be put into the vessel before or after being fixed in the retaining means (12) and should be held by the screw (15) so that the opening of the vessel faces the opening (12a) of the retaining means (12).

A supporting device supports the retaining means (12) so as to move it reciprocally and linearly. A driving system (14) for moving the retaining means is composed of the supporting device and a control device. The supporting device may be any type of device as long as it can move reciprocally and linearly. In this embodiment, the supporting device is constituted with a piston mechanism. More specifically, the retaining means (12) is fixedly connected on the outer surface (12b) of its back wall with the tip of a first piston (16) which is supported by a driving device, such as a first cylinder (17), so that the piston (16) can move linearly and reciprocally in the horizontal direction. The reciprocal linear movement of the retaining means (12) connected with the first piston (16) is accomplished by the first cylinder (17) driven by a driving source, such as electricity or air. In this embodiment, the first cylinder (17) is driven by air and connected with a hose (18) supplying air having a predetermined pressure. Furthermore, the first cylinder (17) is constructed so as to be able to alter the distance and speed of the reciprocal movement of the first piston (16) and mounted releasably onto a first table (19) by means of bolts (20) so as to locate the retaining means (12) at a predetermined height to prevent the table (19) from being in contact with the sealant (11) even though it sags from the opening (12a) of the retaining means (12) to some extent.

The contacting means (13) is in the form of a cylinder and is brought into surface-contacting with the sealant (11) retained in the retaining means (12). The contact means (13) is not restricted in its shape as long as it can apply shear stress on the sealant (11). For example, the contacting surface of the contacting means (13) may be only cylindrical shaped or it may be entirely polygonal shaped. The size of the contacting means (contacting surface) may be arbitrary if it can apply shear stress by contacting the sealant (11) exposed from the opening (12a) of the retaining means (12). It is preferred that the contacting surface (13a) be smaller than the size of the opening (12a) so as to ensure contact with the sealant (11).

The contacting means (13) is supported by means of a piston so as to move reciprocally and linearly, like the retaining means (12). More specifically, the contacting means (13) is fixedly connected at the center of the surface (13b) opposite to the sealant (11) with the tip of a second piston (21) extending in a horizontal relation with respect to the surface (13b). The second piston (21) is supported by a driving device, such as a second cylinder (22), so as to move reciprocally and linearly in the horizontal direction. The second cylinder (22) may be the same as or different from the first cylinder (17). In this embodiment, the second cylinder (22) is the same device as that used for the first cylinder (17) and thus is also connected with a hose (23) supplying air so as to be able to vary the distance and speed of reciprocal movement of the second piston (21).

The second cylinder (22) is also releasably mounted on a second mounting table (25) by means of bolts (24). Table (25) is provided with a positioning mechanism which can adjustably position the cylinder (22), so that the retaining means (12) can be positioned so as to be brought into contact with the contacting means (13) by aligning the second piston (21) with the first piston (16) on the same axial direction.

The second table (25) is provided with a control device (26). The control device (26) moves the retaining means (12) and/or the contacting means (13) so as to apply desirable shear stress on the sealant (11) by controlling the volume of air to be supplied to the first and second cylinders (17,22). Specifically, three types of modes of applying shear stress are selectively conducted. Such modes are as follows:

(a) by moving only the contact means (13),
(b) by moving only the retaining means (12), and
(c) by moving both the retaining means (12) and the contacting means (13).

In the case of mode (a) being selected, the contacting means (13) is brought into contact with the sealant (11) that has been in the retaining means (12), shifted into position, and then is moved reciprocally and linearly a predetermined number of times for a predetermined periods of time, followed by moving at the same time the retaining means (12) and the contacting means (13) in the opposite direction to separate them from each other. In mode (b) the contacting means (13) is shifted into position and thereafter the retaining means (12) is shifted so that the sealant therein is brought into contact with the contacting means (13), followed by moving the retaining means (12) reciprocally a predetermined number of times for a predetermined period of time and then moving at the same time the retaining means (12) and the contacting means (13) in the opposite direction to separate them from each other. In mode (c), the retaining means (12) and the contacting means (13) are shifted to contact each other and then moved reciprocally a predetermined number of times for a predetermined period of time, followed by moving the retaining means (12) and the contacting means (13) in the opposite direction to separate them from each other. In these modes, the maximum distance between the retaining means (12) and the contacting means (13) during the reciprocal movement of the retaining means (12) and/or the contacting means (13) is varied depending upon the area of the sealant (11) and the contacting surface (13a) of the contacting means (13). However the distance is selected from a range such that shear stress can be applied on the sealant (11) without breaking it into two pieces. Therefore, the distance is preferably less than 20 mm to avoid such breakage.

The controlling device (26) has a switching function (27) which can change the above described three modes (a), (b), and (c) and a variable means (28) which can alter the distance and speed of reciprocal movement of the retaining means (12) and the contacting means (13), so that the desired degree of shear stress can be applied on the sealant (11) by selecting the distance and speed of reciprocation of the retaining means (12) and the contacting means (13) in a selected mode. For instance, the sealant (11) can be evaluated in the sagging conditions of the sealant (11) after applying shear stress 150 times for 30 seconds at the distance of the reciprocal movement of 20 mm. In this embodiment, the controlling device (26) is provided in the mounting table (25), but may be provided in the first table (19) or another site.

To evaluate the sagging conditions of a sealant (11) using the apparatus shown in FIG. 1, the sealant (11) is put into a vessel to an extent that it overflows from the vessel and then is scalped with a spatula so as to be level with the edge of the vessel. The vessel is fixed in the retaining means (12) with the opening of the vessel facing the contacting means (13). The contacting means (13) connected with the second piston (21) is positioned so that it is aligned with the first piston (16) and then can be brought into contact with the retaining means (12) by a positioning mechanism.

The retaining means (12) and the contacting means (13) are moved by the driving device (14) after setting the conditions of applying shear stress with the switching device (26) and the variable means (27) for which instance shear stress is applied on the sealant (11) by moving only the contacting means (13) (mode (a)) at a distance of reciprocal movements of 20 mm, 150 times for 30 seconds. Furthermore, other parameters such as temperature affecting the sealant (11) may be optionally selected.

After setting the conditions, the retaining means (12) is shifted by the first piston (16) toward the contacting means (13) which is shifted towards the retaining means by the second piston (21) so that the contact surface (13a) of the contacting means (13) is brought into contact with the sealant (11) in the retaining means (12). After contact, the contact means (13) moves reciprocally 150 times for 30 seconds. The sealant (11) is applied with shear stress by the expansion and contraction of the sealant adhered to the contacting means (13) and the retaining means (12) resulting from the reciprocal movement thereof and leading to the occurrence of breakage in thixotropy. In this way, shear stress can be applied merely by the reciprocal movement of the contacting means (13).

Immediately after completion of the reciprocal movement of the contacting means (13), the retaining means (12) and the contacting means (13) are separated from each other by moving them at the same speed and time in the opposite direction, respectively, whereby the sealant (11) adhered to the retaining means (12) and the contacting means (13) is broken into two pieces one of which is adhered to the retaining means (12) and the other of which to the contacting means (13). For example, the sealant adhered to the retaining means sags as shown FIG. 1. In this figure, the sealant adhered to the contacting means is omitted for illustration.

As described above, since the sealant (11) is applied with shear stress and apparently softens upon separation of the retaining means (12) and the contacting means (13), the sagging of such a softened sealant can be observed and can be evaluated in conformity with a real automotive production line. In an actual production line, a sealant is subjected to high pressure with a pump and the like and kneaded by the contact with the inner walls of pipes upon passing therethrough. Therefore, the sealant is applied to an automotive body in the softened state. Furthermore, the state in which the sealant is softened is varied depending upon parameters, such as the length of pipes. In the method according to the invention, the sagging conditions of the sealant can be evaluated in conformity with a real automotive production line by selecting the conditions of applying shear stress because any degree thereof can be applied on a sealant by changing the settings of the switching function (27) and variable means (28). Alternatively, it is possible to evaluate the sagging conditions of a sealant in better conformity with the intended conditions by setting other parameters affected on the properties of a sealant, such as temperature.

In the following procedure, the sagging conditions of the sealant (11) are evaluated by observing the shape of the sagging sealant. The shape in the sagging state (bead shape) is evaluated by calculation from a length (a) (bead height) indicated by the distance from the center of the opening (12a) of the retaining means (12) to the tip of the sealant (11) extending in the horizontal direction and a length (b) (webbing) of the sealant (11) indicated by the distance from the center of the opening (12a) to the tip of the sealant (11) extending downwardly therefrom in accordance with the following formula:

$$\text{Total Evaluation} = \text{Bead height (a)} \times \text{Bead height (a)} \div \text{Webbing (b)}$$

By using the formula, the sagging conditions can be numerised in a single procedure to discover the degree to which the sealant can maintain the shape.

More specifically, the evaluation using the formula was conducted for Sealants (A), (B), and (C) with the results indicated in Table 1. The measurement was conducted under conditions where shear stress was applied on each of the Sealants (A), (B), and (C) held in the retaining means 150 times at temperature of 20° C. and 25° C. for 30 seconds by reciprocating the retaining means at a distance of 20 mm with pressures of 2 kg/cm² and 1 kg/cm² exerted from the first cylinder to be brought into contact with the sealant. For the purposes of comparison, there was conducted a method in which shear stress is applied manually.

The test apparatus (10) according to the invention can evaluate a sealant in the sagging conditions in a practical manner, because the same level of shear stress can always be applied on the sealant and thus individual variations in evaluation can be avoided even though a plurality of operators participate in the measurement. The inventive apparatus (10) can provide more precise evaluation of the sagging conditions of a sealant because of the capability of indicating the differences in the conditions of measurement such as temperature and pressure exerted by a cylinder.

Furthermore, a sealant can be evaluated in the sagging conditions practically by numerising the results and thus the quality of the sealant can also be numerised, leading to capability of comparison with other sealants. Upon research and development of a novel sealant, the sagging conditions of conventional sealants can be used as an index leading to development of a sealant which is improved in the sagging conditions.

TABLE 1

| Temperature | 1st Cylinder | Material of Sealant | Test Apparatus | | | Hand Shear | |
|---|---|---|---|---|---|---|---|
| | | | bead height | webbing | Total Evaluation | | |
| ° C. | kg/cm | Sealant | (mm) | (mm) | ※ | Flow | Webbing |
| 25 | 2 | A | 13 | 75 | 2 | Δ | X |
| | | B | 17 | 54 | 5 | ○ | X |
| | | C | 22 | 4 | 121 | ◉ | ◉ |
| 20 | 2 | A | 12 | 72 | 2 | Δ | X |
| | | B | 15 | 73 | 3 | ○ | X |
| | | C | 21 | 17 | 26 | ◉ | ◉ |
| | 1 | A | 12.5 | 73 | 2 | | |
| | | B | 16 | 51 | 5 | | |
| | | C | 21 | 15 | 29 | | |

※ Total Evaluation = bead height × bead height ÷ webbing

What is claimed is:

1. A method for evaluating the sagging conditions of a sealant having thixotropy, comprising holding said sealant in a retaining means having an opening through which said sealant is filled and facing in a horizontal direction, bringing the sealant in the retaining means into contact with a contacting means, applying shear stress to said sealant by reciprocal linear movement of said contacting means for a predetermined number of times for a predetermined period of time, separating said retaining means and said contacting means from each other and thereafter examining the shape of said sealant to which shear stress has been applied.

2. The method of claim 1, wherein said retaining means also moves reciprocally and linearly toward and away from said contacting means during application of shear stress to said sealant.

3. A method for measuring the sagging conditions of a sealant having thixotropy, comprising holding said sealant in a retaining means having an opening through which said sealant is filled and facing in the horizontal direction, bringing the sealant in the retaining means into contact with a contacting means, applying shear stress to said sealant by reciprocal linear movement of said retaining means for a predetermined number of times for a predetermined period of time, separating said retaining means and said contacting means from each other and thereafter examining the shape of said sealant to which shear stress has been applied.

4. The method of any one of claims 1–3, wherein the maximum distance of separation of said retaining means and said contacting means from each other during reciprocal movement of said contacting means and/or said retaining means is less than 20 mm.

5. The method of any one of claims 1–3 wherein the shape of said sealant is examined by measuring a length corresponding to the distance from a center of said opening of said retaining means to a tip of said sealant extending horizontally and a length corresponding to the distance from a center of said opening to a tip of said sealant extending downwardly therefrom.

6. An apparatus for measuring the sagging conditions of a sealant which comprises: a retaining means supported so as to be capable of reciprocal linear movement in the horizontal direction and including an opening facing one of the directions of the reciprocal movement, said sealant being held in said retaining means; a contacting means supported so as to be capable of reciprocal linear movement on an extension of the line along which said retaining means moves and being brought into contact with said sealant held in said retaining means; and a driving device for moving said retaining means and/or said contacting means reciprocally and linearly so as to apply shear stress to said sealant and then for separating said retaining means and said contacting means from each other.

7. The apparatus of claim 6, including a switching means having a first position to cause said driving device to linearly reciprocate only said retaining means, a second position to cause said driving device to linearly reciprocate only said contacting means, and a third position to cause said driving device to linearly reciprocate both said retaining means and said contacting means.

8. The apparatus of claim 6 or 7, including means for varying the distance and speed of reciprocal movement of said retaining means and/or said contacting means.

* * * * *